US006042537A

United States Patent [19]

Kaiser

[11] Patent Number: 6,042,537

[45] Date of Patent: Mar. 28, 2000

[54] METHOD AND APPARATUS FOR TISSUE ENLARGEMENT

[76] Inventor: Daniel Kaiser, 2705 Stafford Blvd., Bettendorf, Iowa 52722

[21] Appl. No.: 08/915,540

[22] Filed: Aug. 13, 1997

[51] Int. Cl.[7] .......... A61F 5/00

[52] U.S. Cl. .......... 600/38; 601/14

[58] Field of Search .......... 600/38–41; 128/897; 601/6–14

[56] References Cited

U.S. PATENT DOCUMENTS

| | | | |
|---|---|---|---|
| 3,382,867 | 5/1968 | Reaves | 601/14 |
| 5,228,431 | 7/1993 | Giarretto | 601/11 |
| 5,243,968 | 9/1993 | Byun | 601/11 |
| 5,307,791 | 5/1994 | Senoue et al. | 601/11 |
| 5,536,233 | 7/1996 | Khouri | 600/38 |

*Primary Examiner*—John P. Lacyk
*Attorney, Agent, or Firm*—Rockey, Milnamow & Katz, Ltd.

[57] ABSTRACT

An apparatus and method for enlargement of soft tissue, such as breast, including a vessel or dome configured to fit over the tissue which is to be enhanced or enlarged. The dome or vessel has a sealing cushion of elastic material which surrounds and encompasses the perimeter of the base of the vessel. The cushion includes a fluid compartment which is compressible. The fluid compartment is deformable such that when the vacuum is applied to the sphere, the seal material and compartment deform, isolate, and diffuse the pressure on the skin. The apparatus also includes a vacuum pump with a power source, a pressure sensor to regulate the pressure, or vacuum provided by the pump. The dome also includes a valve mechanism for controlling the ingress and egress of the vacuum to the interior of the dome. This valve will automatically close so that the pump may be removed from the dome and the pressure or vacuum therein be maintained. This valve also includes a release mechanism to remove or exhaust the vacuum in case of discomfort or emergency. The domes may also have different configurations, including rectangular, though normally they will remain as a sphere to maximize and equalize the augmentation of the flesh or tissue within the confines of the dome. The dome also is formed with a footed rim which is embedded in a deformable elastic cushion with a fluid pocket to augment the deformation and consequent reduction in the per square inch pressure applied to the tissue of the wearer.

38 Claims, 3 Drawing Sheets

Fig. 4
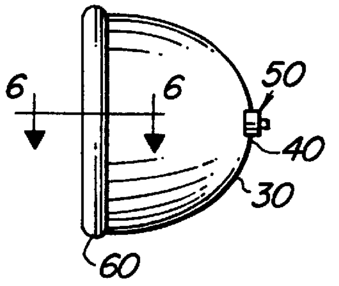
Fig. 5
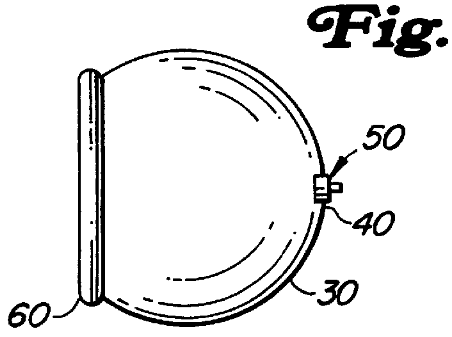
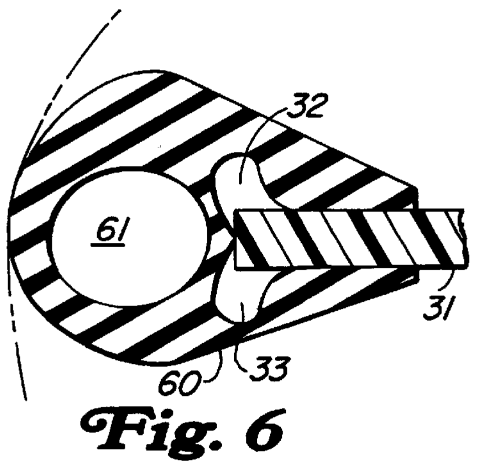
Fig. 6
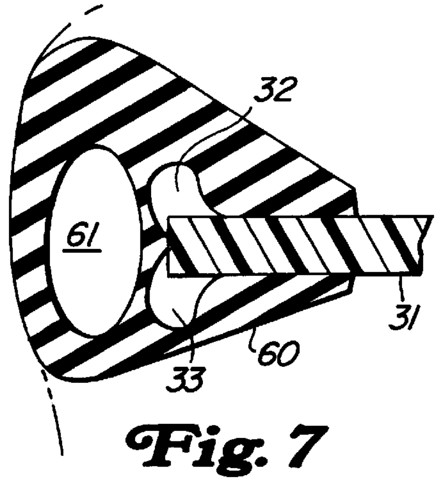
Fig. 7
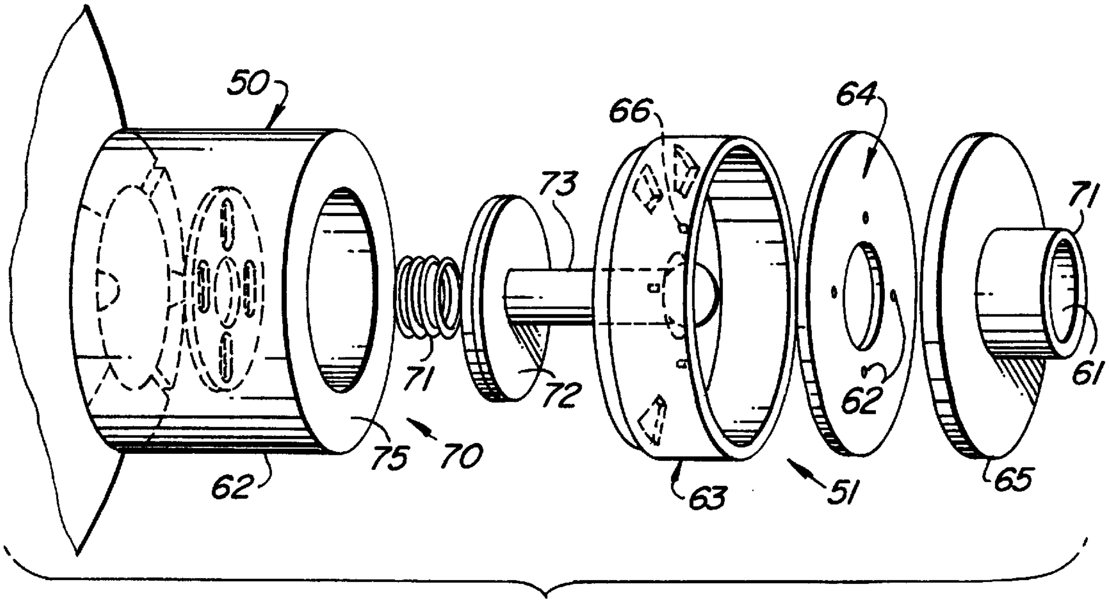
Fig. 8

METHOD AND APPARATUS FOR TISSUE ENLARGEMENT

BACKGROUND AND BRIEF SUMMARY OF THE INVENTION

Field of the Invention and Related Art

Enlargement or enhancement of tissue and especially soft tissue on a person's body is often desirable and may also be necessary to correct abnormalities or improve healing. The improvement or enlargement of breast tissues is an example of one such enlargement.

A safe non-invasive method of soft tissue enlargement, such as breast enhancement, is needed. A safe method and/or apparatus is necessary, especially after the recent problems with implants.

There has long been an understanding of how soft tissue enlargement can occur in nature, i.e., the expansion of the skin during pregnancy and other parts of body accommodate internal growth including subcutaneous growths, as well as weight loss and/or gain.

Prior art devices and methods include surgical techniques, including insertion of balloons and pins for limb lengthening. A thorough review of this prior art is set forth in U.S. Pat. No. 5,536,233 as the basis for the improvement described therein. The generalized method and apparatus described in U.S. Pat. No. 5,536,233 is an improvement over the prior art and describes the basis for the improved invention described hereon.

The prior art has disclosed that the soft tissue enlargement by means of vacuum should occur. However, the prior art did not describe apparatus or vacuum valve which would provide the controlled tissue enlargement on various parts of the body. This invention produces a permanent enhancement of tissue, especially soft tissue, without surgical or other deleterious effects on the patient.

The prior art describes the use of a vacuum to produce soft tissue enlargement. As noted in U.S. Pat. No. 5,536,233, the prior art failed to achieve long term soft tissue enlargement without damage to the soft tissue being enlarged, as well as the surrounding tissue. This damage to the surrounding tissue has limited the amount of vacuum which may be applied to the soft tissue for purposes of enhancement or enlargement. The prior art U.S. Pat. No. 5,536,233 has attempted to avoid this damage to surrounding tissue by the use of a rim around the periphery of the dome to which the vacuum is applied. This rim is described as having sufficient surface area so that the pressure applied by the rim is less than or equal to the negative pressure applied to the soft tissue under the dome. By regulating the pressure within the dome to 1½ inches of Mercury (Hg), the damage to the soft tissue is avoided by use of the rim. The prior art is limited to a vacuum with a magnitude of less than 1½ inches of Hg which limits the enhancement.

This invention overcomes that limitation of limiting the pressure which may be utilized for cell enhancement by diffusing, by a novel seal, the excessive pressures that previously would have been applied to the surrounding tissue causing contusions and/or tissue damage.

The normal animal cell, including that of humans, has in general a predefined shape and size. It has been discovered when sufficiently stressed, the cell will increase in size and its external structure will also deviate to accommodate any vacuum or negative force that is applied to the cell. Proper application of vacuum to the cellular structure can induce the cell to replicate and/or accommodate the stress that is applied by the vacuum. The resiliency of cellular membranes and its supporting structure, as noted in the prior art and as discovered in the use of this invention, can be damaged beyond repair by the application of an excessive amount of vacuum. Therefore, it is critical that the amount of vacuum be controlled and limited to avoid damage to the cells, including internal mechanisms and membranes, being subjected to the vacuum as well as the cells in the surrounding tissue. This invention has shown that animal cellular structures can accommodate vacuums from 0.0009 inches of Hg to 15 inches of Hg without destruction of tissue, if properly applied. Above 15 inches of Hg massive destruction of healthy cells occurs. It has been shown that total destruction of the cell membrane and the nucleus by stretching or elongating beyond its physical limits will destroy these cells. Observation indicates that unhealthy cells being less resilient will be destroyed at different pressures so regeneration is not possible as with healthy cells. This may have positive health benefits due to destruction of unhealthy cells and enhancement of healthy cells. Unhealthy cells will destroy at any pressure and care must be taken not to apply even small amounts of vacuum to unhealthy cells. In general, vacuums of above 15 inches of Hg are necessary to destroy most soft tissue cells. However, a dramatic rapid rise in vacuum (decompression) from 0–8 inches of Hg may cause massive cellular damage as exhibited by bruises and contusions.

The body's system can routinely repair most, if not all, damage caused by light to medium amounts of vacuum. This is similar to the repair of minor contusions, discoloration and vascular seepage caused by small amounts of vacuum such as that which can be applied to the skin by the vacuum induced by the mouth. It has been found that the optimum pressure or the optimum vacuum in inches of Hg necessary to produce the desired affect of inducing cellular reproduction or enlargement and the enlargement or enhancement of soft tissue is 10 inches of Hg.

As a result of experiments utilizing this invention it has been recorded that each new generation of cellular growth or enhancement improves the elasticity and toughness of the cell membranes. Observations of the experiments of applicant indicate that the longer cell structure is stressed by applying 25–75% of the safe maximum vacuum in inches of Hg over an extended period of time, new cellular growth is stronger in structure and more resilient. It has also been shown from the experiments that the greater the negative vacuum or pressure up to 10 inches of Hg, that is applied, result in firmer enhanced tissue in a shorter time.

If this method and apparatus is used, i.e., a vacuum of 1–9 inches of Hg, at the beginning of the enhancement process small and superficial contusions or bruising will occur. It has been determined that the comfort level of vacuum should be gradually increased over a period of time, starting from approximately 1–1½ inches of Hg and proceeding to higher values of vacuum to 8.5 to 9 inches maximum. The apparatus upon which tests were conducted would create a vacuum of 10 inches of Hg. This maximum amount is reduced from 10 inches of Hg for the safety affect.

This invention has also been utilized with variations in the configuration of the dome, sphere, or shape of a vacuum applicator and/or containment vessel. Varying the shape of the vacuum applicator varies the forces exerted upon the material or tissue enclosed in the sphere. Thus, the tissue may be elongated, lengthened, or widened by enhancement or expansion within the sphere.

It has also been discovered in the use of the invention that the more tissue under and in proximity to the dome increases the suction force and the rate of enlargement.

Thus, this invention provides for a plurality of vessels or domes with various configurations to control the direction and the rate of cellular enhancement or enlargement.

The vacuum force acts to cause the veins and arteries to engorge carrying with the benefits of increased blood flow which is a beneficial side affect provided by this invention in conjunction with the enlargement. Although this invention has not been utilized, except to produce new and enhanced or enlarged soft tissue structures, it is believed that other uses of vacuum pressure to induce cellular growth would be useful in other areas. This would require the development of new vessels or instruments which could enclose the area or tissues to be repaired while not damaging the surrounding tissue. The increase in blood flow, due to enlargement of blood vessels, would improve the cells and provide more nutrients to damaged areas such as burns. It also may be useful in muscle development and bone tissue development in both gravity and zero (0) gravity environments or would appear to be useful on most any tissue that has morphotic characteristics.

As noted above, the prior art devices have failed to achieve long term soft tissue enlargement while preventing damage to the soft tissue being enlarged, as well as any surrounding tissue. These prior art devices have not been successful because the amount of vacuum necessary to provide successful enlargement of the soft tissue has not been able to be achieved without damage to surrounding tissue. The low vacuum pressure described in the prior art does not provide for adequate enhancement or enlargement of the soft tissue because the amount of pressure was limited by the ability of the device to prevent damage to the surrounding tissue.

This invention allows the use of a method of enclosing soft tissue within a containing device, applying a substantial vacuum to the soft tissue. The downward force of the vacuum is absorbed by the novel seal without damage to the surrounding tissue against which the container reacts. The invention is able to use a vacuum pressure which will enlarge soft tissue at greater pressures than prior art devices.

The novel seal and force diffuser between the vacuum container and the human cells or tissues surrounding the tissues to be enhanced permits the use of a vacuum force which will stimulate cell activity without permanent harm to cells and/or user.

DESCRIPTION OF THE DRAWINGS

FIG. 4—is one embodiment of vessel.

FIG. 5—is another embodiment of vessel.

FIG. 6—is a sectional view of FIG. 4 with no vacuum.

FIG. 7—is a sectional view of FIG. 4 with vacuum applied.

FIG. 8—is exploded view of check valve.

DETAILED DESCRIPTION OF THE INVENTION

Figure 1:
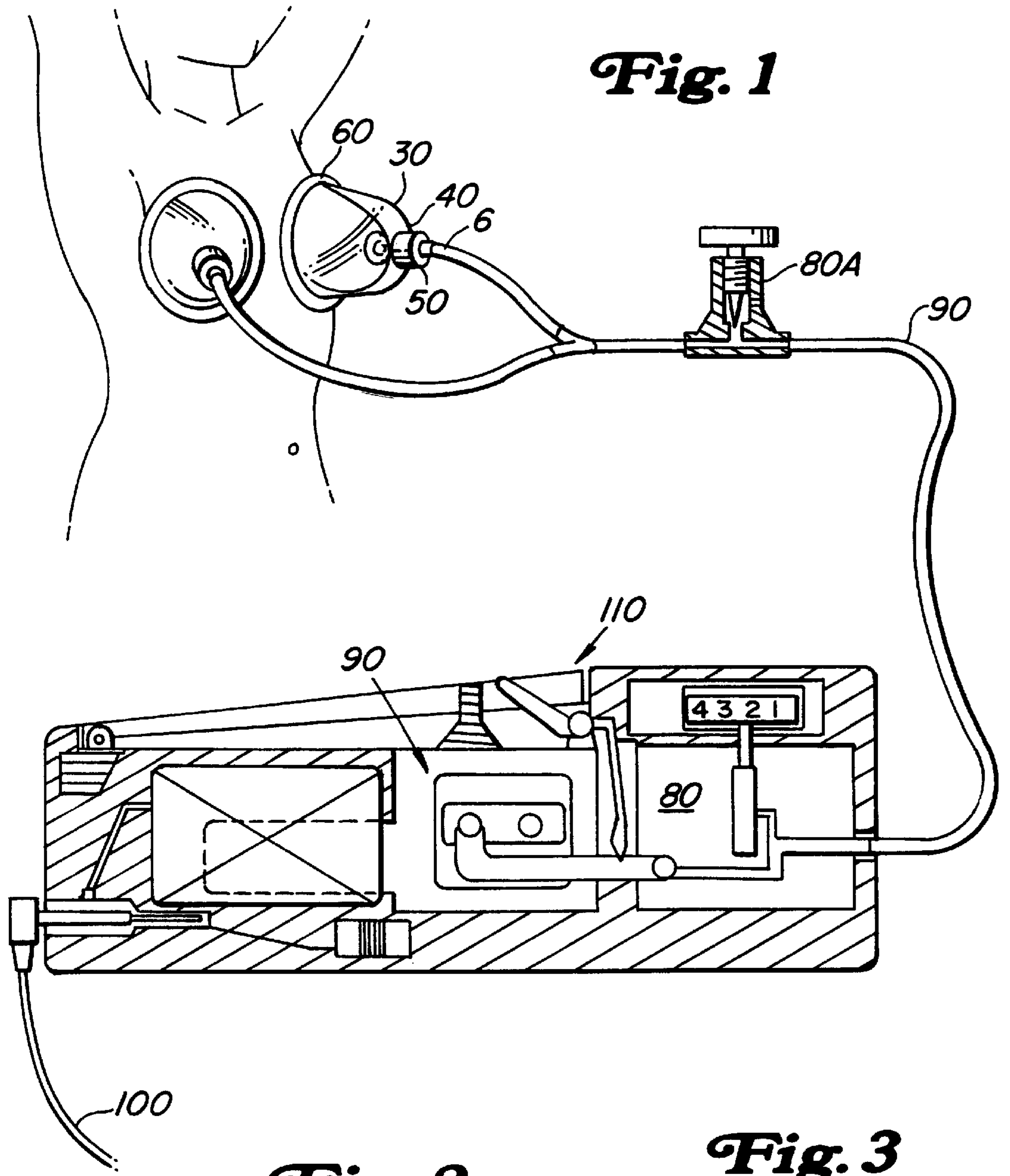
FIG. 1—is a schematic view of the invention.
Figure 2:
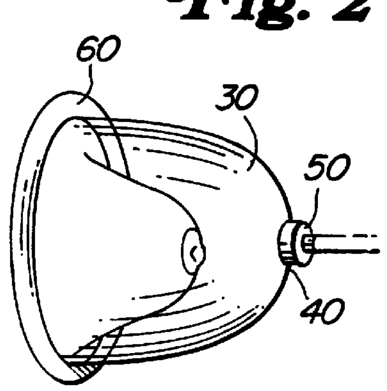
FIG. 2—is a view of vessel, including breast.
Figure 3:
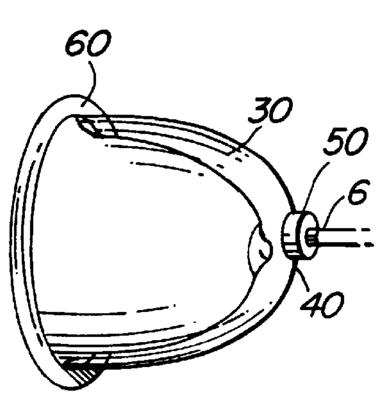
FIG. 3—is a view of vessel with vacuum applied.
Figure 9:
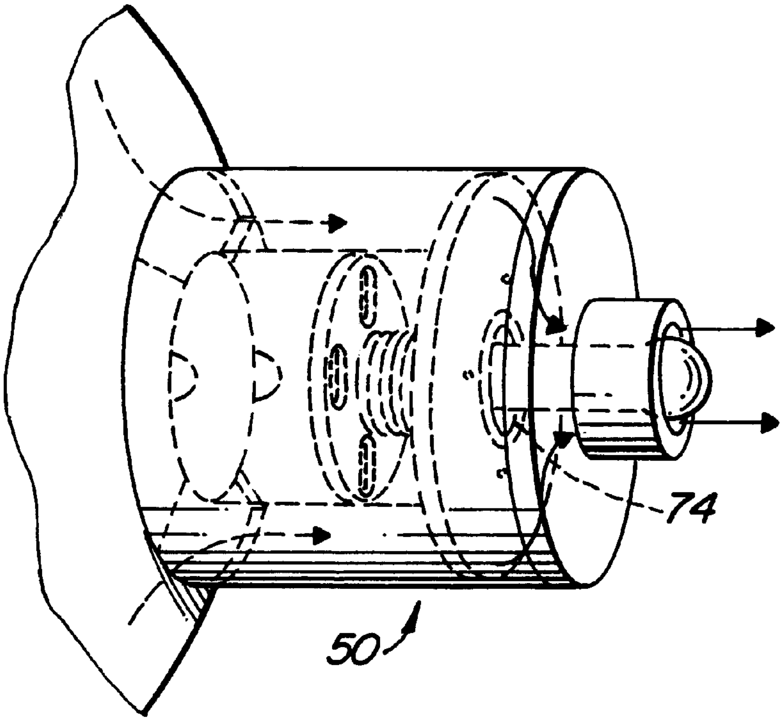
FIG. 9—is check valve in evacuation mode.
Figure 10:
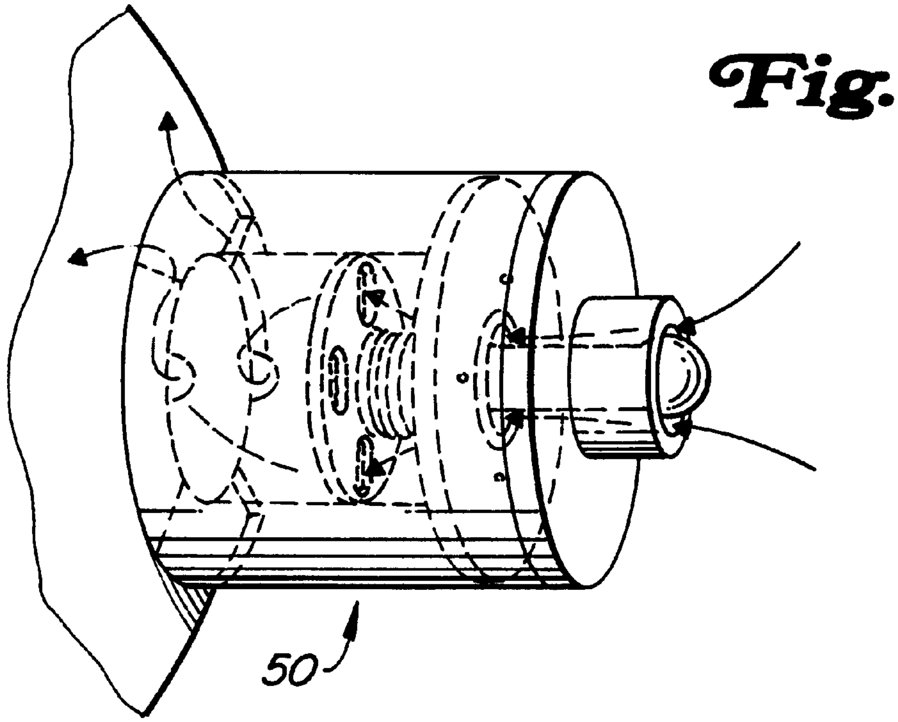
FIG. 10—is check valve in relief mode.

The tissue enhancement apparatus of this invention which provides for the method of enhancement is shown in FIG. 1. This device or apparatus includes a containment vessel or vessels also called domes or biospheres 30. Biospheres 30 have an inlet or outlet 40 which has a novel valve assembly 50 inserted in the inlet or outlet. The sphere 30 also has a sealing cushion 60 surrounding the base of the sphere 30. The sphere 30 is designed to encompass the body portions to be enhanced or enlarged. Relief valve 70 and check valve 51 are incorporated into the valve assembly 50 to permit positive release of the vacuum or at any time it is felt necessary. A source of vacuum, shown as pump 80, is connected by tubing 90 to the spheres 30 and valve assembly 50. A power supply 100 is connected to the control valve 80 through hand control unit 110. Optional external control valve is shown as 80A.

Containment vessels or spheres 30 are made of a material, preferably a plastic, which is hypo-allergenic and resistant to implosion and other destructive forces. In the spheres 30, as utilized, were made of high-impact plastic polymers.

The self-sealing valve 50 inserted in inlet or outlet 40 is designed to hold any vacuum created in the sphere. A relief valve 70 and check valve 51 are included as part of the novel valve mechanism 50 of this invention.

As shown in FIG. 8, the valve 50 includes vacuum inlet 61, which is also exhaust port 71, which releases the vacuum when the relief valve 70 is actuated. Check valve 51 and relief valve 70 comprise one unit, though the valves could be designed to operate separately. The check valve 51 maintains the vacuum by operation of the valve body housing 62, valve body middle cap 63, check valve gasket 64, valve body cap 65, gasket retainer pin 66, and gasket retainer holes 62. The vacuum is applied to the valve by tubing 90 from the vacuum source 80.

The relief valve portion 70 comprises relief valve tension spring 71, seal 72, plunger 73, exhaust port 74, and relief valve body 75.

As shown in FIGS. 6 and 7, the cushion 60 is designed to provide an air tight seal between the sphere 30 and the body of person wearing the sphere 30. The cushion 60 is flexible and waterproof, and includes a built-in air cushion 61. Cushion or seal 60 should be made of flexible material which is resilient and possesses some compressible characteristics. This air cushion 61 could also be a fluid other than air, but one which should be compressible. The air cushion 61 in its uncompressed state is an oval, normally in-line with the sphere surface 31. In this novel mechanism the sphere surface 31 is split into two bevels or flanges 32 and 33 in order to more evenly distribute the forces applied by the vacuum to sphere 30. When the seal 60 is compressed, the air cushion 61 deforms to increase the surface area beneath the sphere 30. This will serve to diffuse and reduce the pressure on the surface to a level which does not cause contusions, i.e., when no more than 10 inches is applied.

The operation of this apparatus and method of cellular enhancement or enlargement will now be described.

The operation of this apparatus will be described with special relationship to the enlargement of the average female having normal healthy breasts. As been noted, the design of the containment vessel or the vessel to which the vacuum is to be applied is of upmost importance. The vessel must be designed to encompass and direct the enlargement or enhancement by the vacuum. The shape of the vessel and the size of the vessel must be coordinated with the mass and shape of the tissue to be enlarged.

It is has been determined that there are several shapes and designs which could be utilized to enhance breast enlargement. The requirement and the importance of the shape of the vessel is that this shape controls the distribution of forces and the direction of the forces by the design of the vessel.

It has been determined from an analysis of the current bra size, including cup shape, from 30 A to 50 DDD. In as much as sizing is critical for shaping and proper and proportional growth, it is necessary for the person to take certain measurements in order to determine the size and shape of the vessel to properly enhance the breast. The first critical measurement is the width of the breast where the outermost part of the breast connects to the chest wall. The next most critical measurement is the cup size in inches for the American market and metrics for the foreign markets. This is done by measuring the widest part of the appendaged breast.

Another critical measurement is the length of the breast from the ribs to the nipple. Then these critical measurements may be used to determine the optimal breast biosphere or vessel for each individual's proper enhancement of the breast. As the breast or soft tissue is permanently enlarged, it may be necessary, not only may but will be necessary, to change the size or design of the vessel. There are three basic designs for the operation of this apparatus. The diameter and height of the vessel or sphere will be changed according to the individual's needs. The basic design for smaller breasts will normally have a diameter range from 3 inches to 9 inches and the height of the vessel may range from 2 inches to 10 inches.

The next basic design would be utilized for people that have a present bra size of 32AAA to 50A and, in this case, the vessel's diameter will range from 3 inches to 12 inches and the height of the vessel will range from 2 inches to 10 inches.

The third basic design would be used by people that have a present bra size of 32C/D to 50D/DD. In this case, the vessel's diameter will range from 3 inches to 12 inches and the height range from 2 inches to 10 inches.

As the breast is enlarged and changed in shape by the use of this apparatus it will become necessary to redefine and remeasure the breast size. This will require a change in the size and shape of the sphere or vessel to continue the enhancement or enlargement of the soft tissue to the desired shape.

Contact area under the cushion 60 and also lubricate at least 2 inches to the outside of the seal's contact point with the skin. This is to ensure that the skin is able to move in response to the vacuum without damage to soft tissue and still maintain the seal. It will be also necessary to moisturize the areola and other breast tissues at the same time to enhance expansion and to facilitate free movement.

The person then places the vessel or biosphere over each breast. The vacuum tubing 90 would then be connected to the valve 50. The other end of the tubing would be connected to the vacuum pump 90 through control unit 80 or 80A. The vacuum control unit is plugged into a power DC supply 100 which is connected to the AC power source.

The control unit 80 or 80A has, for example, a plurality of settings for the pressure of the vacuum. These settings may be low, medium, high, and maximum to allow the user/wearer to set the amount of vacuum to a setting that is most comfortable and/or to maximize the enhancement process. These settings start at low and go to maximum allowed by the control unit 50 or 50A. The pump is then turned on and the setting that is most comfortable for the individual is chosen and the resultant vacuum applied to the biosphere. Once the desired vacuum level has been achieved, which may be called a comfort level, i.e., the person feels comfortable with that amount of vacuum being applied to the breasts, the tubing is removed from the vessel and the built-in check valve 51 holds that pressure.

The wearer is then free to move around. They may place a brazier over the spheres or the spheres are self-supporting and the wearer is free to move around, go to bed, or any other operations which they desire.

The time use of this active process is critical. The more time under vacuum, the faster the results. Excessive use of the process can cause blistering and rob the skin of contact with the normal atmosphere for oxygen and evaporation of body fluids. Through testing it has been found that the process may be used as described below but can also be tailored to the individuals personal needs and lifestyles. The more sensitive the individuals skin is and the rate at which each individual's body heals will have a direct effect on the healthy use of this process.

The recommended process is to start at lowest level of vacuum and slowly build to highest level and utilize the vacuum for 6 to 8 hours every other day. This allows time for the cells to rejuvenate and recuperate from the process. This should be done every other day for 8 days and then let the soft tissue rest for 3 days. Then start the process again with the same routine. Some individuals may use the higher settings sooner than other individuals. These recommendations have been arrived at through experimentation for the average healthy person. Variations may and will take place.

No permanent side effects have been observed during testing.

This process penetrates deeply into the layers of soft tissue and will help to firm and enhance the underlining muscle tissue also.

When the maximum application time is reached or if the wearer becomes uncomfortable and the wearer wishes to remove the vessels, all that is necessary is to depress the release valve and this will automatically release the vacuum in the vessel.

If it is desired to utilize the vessels during a sleep routine, there is an optional cover that can be placed over the relief valve to prevent accidental discharge.

Having described the preferred embodiment, other features of the present invention will undoubtedly occur to those versed in the art, as will numerous modifications and alternations in the embodiments of the invention illustrated, all of which may be achieved without departing from the spirit and scope of the invention as defined in the appended claims.

What is claimed is:

1. An apparatus for enhancing living tissue comprising:

a) a vessel having an open end and adapted to encompass the tissue to be enhanced;

b) a source of vacuum connected to said vessel; and c) a flexible mass affixed to the open end of said vessel to absorb the pressure exerted by said vacuum, thereby acting as a seal and force diffuser between the vessel and the tissue adjacent the periphery of said vessel.

2. The apparatus in accordance with claim 1, wherein said vessel has a shape generally conforming to the shape of the tissue to be enhanced.

3. The apparatus in accordance with claim 1, wherein said vessel has a volume greater than the volume of tissue to be enhanced.

4. The apparatus in accordance with claim 1, wherein said vessel has a shape which is varied to control the shape of the tissue enhanced.

5. The apparatus in accordance with claim 1, wherein said vessel is dome-shaped having a periphery to surrounding the tissue to be enhanced.

6. The apparatus in accordance with claim 1, wherein said vessel has an opening separate from said open end for connection to said source of vacuum.

7. The apparatus in accordance with claim 1, wherein said flexible mass includes an air pocket.

8. The apparatus in accordance with claim 7, wherein said mass and said air pocket are substantially aligned with the centerline of the periphery of the open end of said vessel.

9. The apparatus in accordance with claim 8, wherein said periphery of the open end of said vessel includes flanges on both surfaces of said vessel at angles to the centerline of said periphery.

10. The apparatus in accordance with claim 9, wherein said flanges have an arcuate configuration.

11. The apparatus in accordance with claim 10, wherein said arcuate configuration is convex with respect to the periphery of said vessel.

12. The apparatus in accordance with claim 9, wherein said flange applies the force of the vacuum to the flexible mass and said air pocket to substantially diffuse the force of the vacuum applied at the base of the flexible mass affixed to said vessel.

13. The apparatus in accordance with claim 1, wherein said connection between said vacuum source and said vessel, includes a valve mechanism.

14. The apparatus in accordance with claim 13, wherein said valve mechanism includes a check valve.

15. The apparatus in accordance with claim 13, wherein said valve mechanism includes a relief valve.

16. The apparatus in accordance with claim 13, wherein said valve mechanism includes both a check valve and a relief valve to automatically maintain the vacuum in said vessel and provide instant release of said vacuum.

17. The apparatus in accordance with claim 1, wherein said vessel will withstand a vacuum of 15 inches of Hg.

18. The apparatus in accordance with claim 1, wherein said source of vacuum includes a control mechanism to control the value of the vacuum provided.

19. The apparatus in accordance with claim 18, wherein said control mechanisms will control the vacuum from 0.1 inches of Hg to a maximum of 10 inches of Hg to be applied to said vessel.

20. An apparatus for enlarging living tissue comprising:

a) a vessel having an open end and adapted to encompass the tissue to be enlarged;

b) a source of vacuum connected to said vessel; and c) a mass of elastic material affixed to the perimeter of the open end of said vessel to transform said vacuum applied to create a seal and force diffuser for the forces between the interior of the vessel and the tissue on which said vessel rests.

21. The apparatus in accordance with claim 20, wherein said vessel has a shape generally conforming to the shape of the tissue to be enlarged.

22. The apparatus in accordance with claim 20, wherein said vessel has an interior volume greater than the volume of tissue to be enlarged.

23. The apparatus in accordance with claim 20, wherein said vessel has a shape which is varied to control the configuration of the resultant enlargement.

24. The apparatus in accordance with claim 20, wherein said vessel is dome-shaped and open at one end to encircle the tissue to be enlarged.

25. The apparatus in accordance with claim 20, wherein said vessel has an opening separate from said open end for connection to a source of vacuum.

26. The apparatus in accordance with claim 20, wherein said elastic material surrounds an air pocket.

27. The apparatus in accordance with claim 26, wherein elastic material and said air pocket are substantially aligned with the centerline of the perimeter of the vessel.

28. The apparatus in accordance with claim 27, wherein said perimeter of the open end of said vessel includes flanges at angles to the centerline of said perimeter.

29. The apparatus in accordance with claim 28, wherein said flanges have an arcuate configuration.

30. The apparatus in accordance with claim 29, wherein said arcuate configuration is convex with respect to the perimeter of said vessel.

31. The apparatus in accordance with claim 28, wherein said flanges apply the force of the vacuum to the elastic material and said air pocket to substantially diffuse the force of the vacuum applied to the base of said elastic material.

32. The apparatus in accordance with claim 20, wherein said connection between said vacuum source and said vessel, includes a valve mechanism.

33. The apparatus in accordance with claim 32, wherein said valve mechanism includes a check valve.

34. The apparatus in accordance with claim 32, wherein said valve mechanism includes a relief valve.

35. The apparatus in accordance with claim 24, wherein said valve mechanism includes both a check valve and a relief valve to automatically maintain the vacuum in said vessel and provide instant release of said vacuum.

36. The apparatus in accordance with claim 20, wherein said vessel will withstand a vacuum of 15 inches of Hg.

37. The apparatus in accordance with claim 20, wherein said source of vacuum includes a control mechanism to control the value of the vacuum provided.

38. The apparatus in accordance with claim 37, wherein said control mechanisms will limit the vacuum from 1 inch of Hg to a maximum of 10 inches of Hg to be applied to said vessel.

* * * * *